US005580959A

United States Patent [19]
Cook et al.

[11] Patent Number: 5,580,959
[45] Date of Patent: *Dec. 3, 1996

[54] PURIFICATION OF ZEIN FROM CORN GLUTEN MEAL

[75] Inventors: Richard B. Cook, Revere; Frank M. Mallee, Acton; Mark L. Shulman, Waltham, all of Mass.

[73] Assignee: Opta Food Ingredients, Inc., Bedford, Mass.

[ * ] Notice: The portion of the term of this patent subsequent to Dec. 26, 2011, has been disclaimed.

[21] Appl. No.: 402,320

[22] Filed: Mar. 10, 1995

Related U.S. Application Data

[63] Continuation of Ser. No. 137,702, Oct. 15, 1993, abandoned, which is a continuation of Ser. No. 814,118, Dec. 26, 1991, Pat. No. 5,254,673.

[51] Int. Cl.$^6$ .............................. A23J 1/12; C07K 14/425
[52] U.S. Cl. ............................................. 530/373; 426/656
[58] Field of Search .................................... 530/373, 374, 530/376, 412, 414; 426/656

[56] References Cited

U.S. PATENT DOCUMENTS

| | | | |
|---|---|---|---|
| 1,245,818 | 11/1917 | Takamine et al. | 530/372 |
| 1,280,862 | 10/1918 | Satow | 530/372 |

(List continued on next page.)

FOREIGN PATENT DOCUMENTS

| | | | |
|---|---|---|---|
| 480762 | 1/1952 | Canada | 530/373 |
| 5-23117 | 2/1993 | Japan . | |
| 536024 | 4/1941 | United Kingdom | 530/373 |
| 651396 | 4/1951 | United Kingdom | 530/373 |

OTHER PUBLICATIONS

Chemical Abstract 102:44547n (1985).
Mason, I.D. and Palmer, L.S., "Preparation of White Zein From Yellow Corn", *J. Biol. Chem.*, 107:1321–132 (1934).
Dill, D.B., "The Behavior of the Prolamins in Mixed Solvents. II.", *J. Biol. Chem.*, 72:239–247 (1927).
Manley, R.A. and Evans C.D., "The Critical Peptization Temperature of Zein in Concentrated Ethyl Alcohol", *J. Biol. Chem.*, 143:701–702 (1942).
Manley, R.H. and Evans, C.D., "Binary Solvents for Zein", *Ind. Eng. Chem.*, 351:661–665 (1943).
Vitale, A., et al., "Reduced Soluble Proteins Associated with Maize Endosperm Protein Bodies", *J. Exp. Botany*, 33:439–448 (1982).
Larkins, B.A., et al., "The Zein Proteins of Maize Endosperm", *TIBS*, 306–308 (1984).
Larkins, B.A., et al., "19. Structural Analysis and Modification of Maize Storage Proteins", *J. Industrial Micro.*, 30:Supp 4, 203–209 (1989).
Schnarrenberger, C., et al., "Isolation of Protein Bodies on Sucrose Gradients", *Planta*, 104:185–194 (1972).
Harris, P.L., et al., "Lipid and Color Evaluations of Solvent-Extracted Maize Gluten Meal", *Cereal Chem.*, 64:283–284 (1987).

*Primary Examiner*—Jeffrey E. Russel
*Attorney, Agent, or Firm*—Hamilton, Brook, Smith & Reynolds, P.C.

[57] ABSTRACT

This invention pertains to methods for extracting and purifying zein, zein bodies, glutelins or destarched corn gluten from corn gluten meal by efficiently removing and recovering food grade pigments and starch hydrolysates, while discarding unwanted fractions. Corn gluten is subjected to the combination of enzymatic starch hydrolysis, alkaline treatment, alcohol washing and alcohol extraction to produce a substantially starch-free, deflavored and decolored zein which is suitable for use in foods and pharmaceuticals. An advantage of the process described herein is its use of food grade alcohol(s) to deflavor, decolorize and extract the zein from corn gluten meal. Purified zein and zein bodies have improved utility and functionality in a variety of existing and emerging food applications. Alternate products such as deflavored, decolored and destarched corn gluten, zein bodies or glutelins are also obtained by the methods of this invention and are useful as vegetable protein supplements. By-products of the invention such as yellow food pigments and starch hydrolysates can be further purified and/or used directly in various foods.

13 Claims, 4 Drawing Sheets

U.S. PATENT DOCUMENTS

| | | | |
|---|---|---|---|
| 2,044,769 | 6/1936 | Buron et al. | 530/373 |
| 2,105,760 | 1/1938 | Swallen | 530/373 |
| 2,120,946 | 6/1938 | Swallen | 530/373 |
| 2,133,591 | 10/1938 | Swallen | 530/373 |
| 2,156,928 | 5/1939 | Swallen | 530/373 |
| 2,206,310 | 7/1940 | Swallen | 530/373 |
| 2,221,560 | 11/1940 | Swallen | 530/373 |
| 2,229,870 | 1/1941 | Pearce | 530/373 |
| 2,238,591 | 4/1941 | Horesi et al. | 530/373 |
| 2,272,488 | 2/1942 | Swallen | 530/373 |
| 2,287,649 | 6/1942 | Swallen | 530/373 |
| 2,332,356 | 10/1943 | Swallen | 530/373 |
| 2,355,056 | 8/1944 | Coleman | 530/373 |
| 2,360,381 | 10/1944 | Walsh | 530/373 |
| 2,479,519 | 8/1949 | Schopmeyer | 530/376 |
| 2,554,750 | 5/1951 | Pinner et al. | 530/373 |
| 2,676,169 | 4/1954 | Baldoni | 530/373 |
| 2,733,234 | 1/1956 | Morris | 530/373 |
| 2,882,265 | 4/1959 | Morris et al. | 530/373 |
| 3,535,305 | 10/1970 | Carter et al. | 530/373 |
| 3,782,964 | 1/1974 | Knight | 530/374 |
| 3,802,896 | 4/1974 | Westall et al. | 524/17 |
| 3,880,665 | 4/1975 | Himmelmann | 530/354 |
| 4,018,936 | 4/1977 | Garbutt et al. | 530/374 |
| 4,100,151 | 7/1978 | Adler-Nissen | 530/374 |
| 4,624,805 | 11/1986 | Lawhorn | 530/376 |
| 4,645,831 | 2/1987 | Lawhon | 530/414 |
| 4,716,218 | 12/1987 | Chen et al. | 530/372 |
| 5,021,248 | 6/1991 | Stark et al. | 530/373 |
| 5,254,673 | 10/1993 | Cook et al. | 530/373 |
| 5,367,055 | 11/1994 | Takahashi et al. | 530/373 |

PURIFICATION OF ZEIN FROM CORN GLUTEN MEAL

This application is a continuation of application Ser. No. 08/137,702 filed Oct. 15, 1993, now abandoned, which is a continuation of U.S. Ser. No. 07/814,118, filed Dec. 26, 1991 (issued as U.S. Pat. No. 5,254,673 on Oct. 19, 1993).

BACKGROUND OF THE INVENTION

A primary by-product of commercial corn wet milling is wet corn gluten meal (CGM) which is typically concentrated and sold in dry form (approximately 90% solids). CGM is known to be most stable in dry form. Zein can be readily obtained by further processing of corn gluten meal. The potential yield of zein is about one pound per bushel of corn.

Corn gluten has been processed into varying grades of zein depending upon the particular end use, i.e., for use in plastics, protective coatings, inks, food products, pigments, adhesives and films, among other uses. In food applications, the quality of the zein is of paramount importance to the overall organoleptic properties of the food product. For instance, currently available grades of zein contain impurities that can impart off-flavors and colors (particularly yellow color—due to the presence of xanthophyll and carotene pigments) to the food product. Further processing of the zein to remove undesirable colors and off-flavors has been developed with limited success, particularly for use in foods.

Processes for producing "white" zein by extraction with ethylene dichloride (Mason and Palmer, *J. Biol. Chem.* 107:131–132 (1934)), benzene (U.S. Pat. No. 2,133,591 issued to Swallen) and other hydrocarbons (U.S. Pat. Nos. 2,287,649 and 2,272,488 both issued to Swallen; U.S. Pat. No. 2,229,870 issued to Pearce) have been described. Although the product has minimal color, the use of these solvents make the "white" zein unacceptable for use in the food and pharmaceutical industry.

Enzymatic modification of corn gluten by proteolytic hydrolysis to produce a flour-like material was previously described by Adler-Nissen (U.S. Pat. No. 4,100,151). Enzyme hydrolysis of crude gluten using alpha-amylase has also been described by Knight (U.S. Pat. No. 3,782,964). In both of these processes, the product generated is a modified gluten rather than zein.

Alcohol extraction of corn gluten to obtain zein has been described by Lawhorn (U.S. Pat. No. 4,624,805), Chen and Hoff (U.S. Pat. No. 4,716,218), Coleman (U.S. Pat. No. 2,355,056), Carter and Reck (U.S. Pat. No. 3,535,305) and Swallen (U.S. Pat. Nos. 2,287,649, 2,332,356, 2,105,760, 2,120,946, 2,133,591 and 2,272,488). In each instance, zein is extracted using a solvent (e.g., ethanol, isopropanol) and concentration for which zein is soluble therein. The extracted zein produced by these methods tend to contain impurities that are coextracted and soluble in the extraction solvent. Further extraction of the impurities is necessary to adequately depigment and deflavor the zein product.

Thus, it is desirable to process corn gluten to generate a purified, food grade zein that is essentially decolored, deflavored and odor-free and suitable for use in food and pharmaceutical applications.

SUMMARY OF THE INVENTION

This invention pertains to methods for purifying, fractionating and recovering zein, zein bodies, glutelins and mixtures thereof from corn gluten meal. Purification involves removing and recovering food grade pigments, glutelin(s) and starch hydrolysates, while discarding unwanted fractions. Corn gluten is subjected to a combination of enzymatic starch hydrolysis, alkaline treatment, alcohol washing and either deflavored, decolored alcohol extraction of the deflavored and decolored zein or fractionation of the resultant deflavored, decolored gluten into zein body or glutelin components. The deflavored and decolored zein is suitable for use in foods and pharmaceuticals. An advantage of the process described herein is its use of food grade alcohol(s) to deflavor, decolor and extract the zein from corn gluten meal. Purified zein and zein bodies have improved utility and functionality in a variety of existing and emerging food applications. By-products such as glutelins, pigments and starch hydrolysates are also obtained by the methods of this invention and can be further purified for use as natural food colors and vegetable protein supplements. Alternatively, zein bodies may be harvested separate from glutelins or admixed with them in various proportions as deflavored and decolored corn gluten.

DETAILED DESCRIPTION OF THE INVENTION

This invention pertains to methods for purifying zein from corn gluten meal, a major by-product of wet corn milling. Either a wet or gently dried gluten can be used as the starting material for the methods of this invention. The term "wet corn gluten" refers to an aqueous mixture of corn gluten that is muddy in appearance and contains from about 10–50% solids (e.g., from about 50 to about 75% protein and from about 15 to about 30% starch). Wet corn gluten also contains an amount of sulfite (approx. over 1,000 ppm dry weight) which is beyond the maximum permissible level for most foods, (100 ppm limit for shrimp, for example). The term "dry corn gluten" refers to a corn milling by-product that has been further processed to reduce its moisture content to stabilize the corn gluten against degradation. This form of gluten, however, should be gently dried under conditions which preserve zein body membranes and spheroidal shape. Typically dry corn gluten (also referred to as "commercial corn gluten") contains about 90% solids. Wet or gently dried forms of corn gluten that deviate from the above description are included within the scope of this invention. The wet form of gluten is preferred for the purpose of this invention because the expense of drying and the generation of off-flavors associated with high temperature (90°–400° C.) conventional drying are eliminated. However, the quality of wet gluten for the purpose of this invention, will deteriorate after a few weeks if it is not stored frozen. In comparison, commercial (or dry) CGM which has heretofor been the preferred raw material for obtaining commercial zein, offers the advantage of improved microbial stability and shelf life at ambient temperature.

Figure 1:
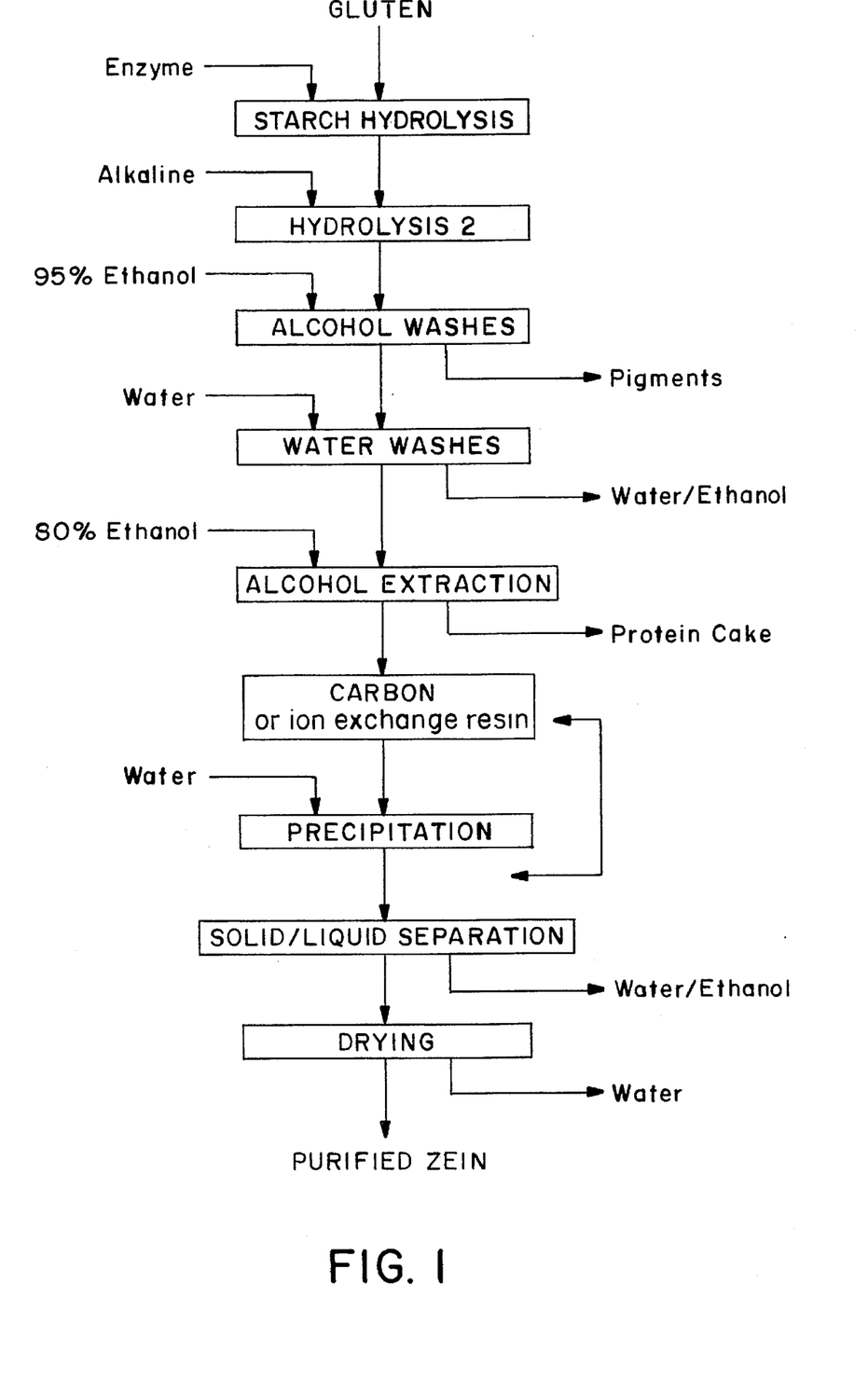
FIG. 1 is a schematic representation of the zein purification process of this invention.

According to this invention, corn gluten meal (either wet or gently dried forms) is subjected to a series of treatments which include enzymatic digestion of starch, alkaline removal of hydrocarbons and off-flavors, separate pigment and zein extraction with alcohol, leaving glutelin, alcohol washes, extractions and centrifugal separation to remove pigments, glutelin(s), residual starch and hydrocarbons, to thereby yield deflavored and decolored zein. These contaminants contribute colors, off-flavors and odors to zein. In the broadest aspect of the invention, deflavored and decolored zein or zein bodies and glutelins are produced from corn gluten by first removing color and flavor impurities from the gluten using an aqueous alcoholic solvent having a concentration which does not substantially extract the zein, zein bodies and glutelin therefrom. The alcohol concentration is then changed to separate the gluten into deflavored and decolored zein or zein bodies and glutelin fractions. FIG. 1 schematically illustrates the steps employed to purify zein from wet or gently dried corn gluten. Each of these steps are specifically described in detail below.

Wet or gently dried corn gluten, obtained either from a commercial source or directly from a wet milling product stream, is first subjected to enzymatic treatment to hydrolyze residual starch in the corn gluten. Complete digestion and removal of starch from the gluten substantially improves the effectiveness of the subsequent decoloring and deflavoring steps due, in part, to proximity of starch granules, zein bodies and glutelins in the corn gluten. Enzymatic hydrolysis is accomplished primarily through the action of α-amylase. In addition to α-amylase, this step can be performed using a combination of other carbohydrate hydrolyzing enzymes, such as glucoamylase, pullulanase or cellulase. The destarching step can be optimized by first homogenizing or agitating the corn gluten meal suspension to adequately separate and disperse the particles. Brief homogenization should be employed when wet CGM is used. Homogenization, however, is especially necessary when dry corn gluten is used as the starting material. Care should be taken to avoid harsh homogenization conditions (e.g. high pressure homogenizers) that can rupture the native structure of cell-like or sub-cellular organelles, such as zein body membranes.

By-product starch hydrolysates can be recovered from the discarded portion and further processed and/or purified. The yield of carbohydrate by-product can be further increased by hydrolyzing the fiber portions of CGM or by increasing the glucose content by addition of other polysaccharide depolymerase enzymes. The pH, temperature and time are chosen to achieve the optimal enzyme activity using known techniques and specifications.

The destarched corn gluten is then treated with a mild alkaline buffer (i.e., pH 7.5 to 9) to improve removal of fatty acids and residual corn oils from the enzyme hydrolyzed corn gluten. Alkaline treatment further aids in removal of compounds from the corn gluten which impart its characteristic strong, bitter off-flavor. This step is performed using sodium or potassium carbonate/bicarbonate at a pH of from about 8 to about 9 and a temperature of from about 60° to about 80° C., preferably 80° C. Other mild alkaline solutions can be used such as sodium hydroxide, calcium hydroxide or potassium hydroxide, provided that the pH does not exceed about 9. Very little or substantially none of the xanthophyll, zeanthophyll and carotene natural food pigments are solubilized at this stage. This permits subsequent alcohol extraction and recovery of these pigments under conditions which insure their native structure, minimize high alkaline-induced by-product formation (i.e., pH>9) and minimize zein solubilization. Aqueous washing between the enzymatic hydrolysis and alkaline treatment steps removes most of the carbohydrate that may form flavor and color compounds. After alkaline treatment, the pH can be lowered (e.g., from about pH 6.5 to about 7.5) by adding a suitable organic or inorganic acid (e.g., acetic acid or HCl) with good mixing.

Figure 2:
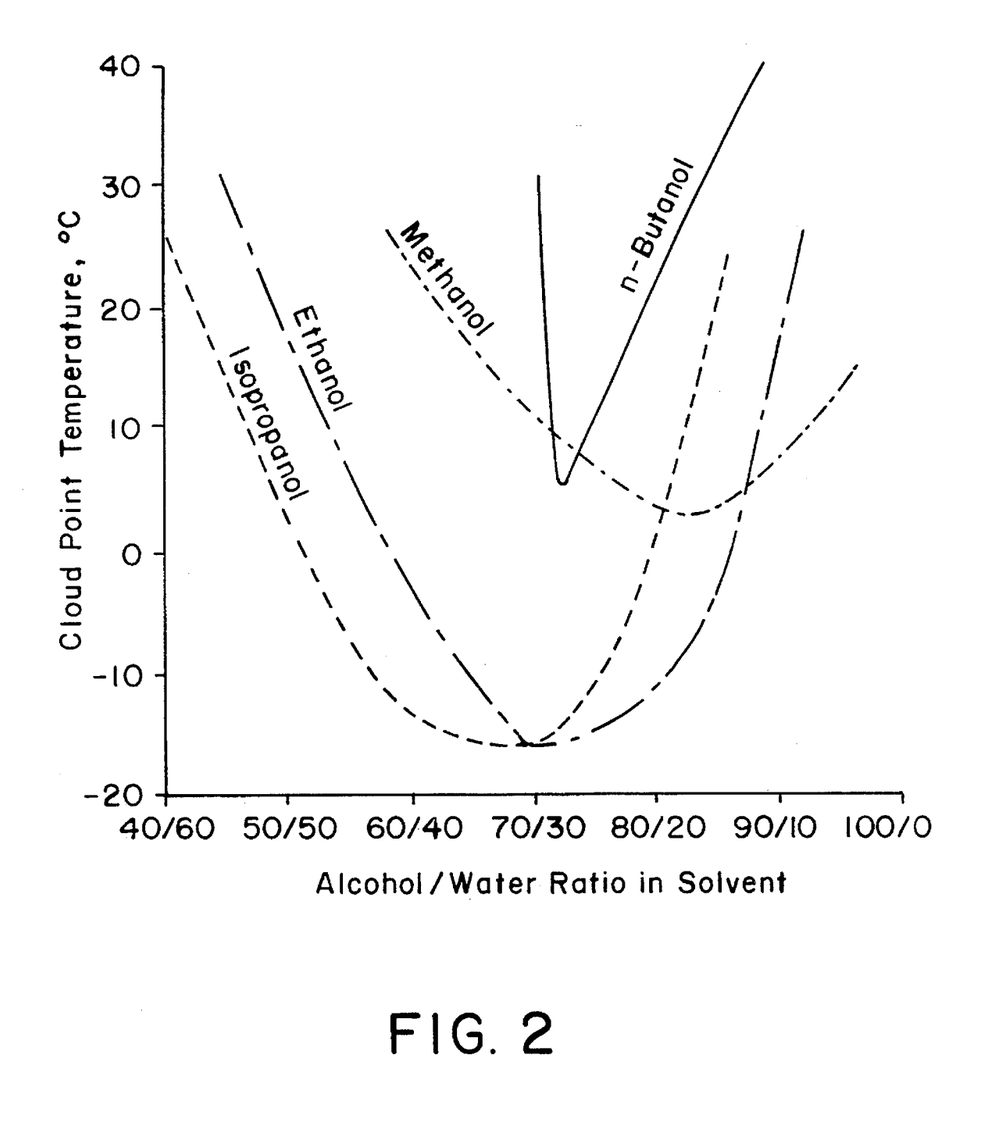
FIG. 2 is a graphic representation of cloud point temperatures for 30% zein solutions in varying concentrations of aqueous alcohol (e.g., ethanol, methanol, isopropanol and n-butanol). R. A. Reiners, et al., "Corn Proteins: Potential For Their Industrial Use", 58th American AOCC Meeting, St. Louis, Mo., Nov. 4, 1973.

After enzyme hydrolysis and alkaline treatment, the resulting gluten will still contain glutelin(s), pigments, zein(s) and various hydrocarbons. This form of gluten is then decolored and further deflavored by a series of alcohol washes to harvest natural food colorants and simultaneously remove minor residual off-flavor from the gluten. The concentration of alcohol is chosen to specifically solubilize pigments and flavoring agents but not substantially solubilize the zein portion. The solubility of a given zein component of CGM can be ascertained by selecting conditions (i.e., alcohol concentration and temperature) at which zein is not extracted along with the impurities. See FIG. 2 which graphically illustrates how alcohol temperature and titer affect zein solubility. As shown in this Figure, room temperature (about 25° C. neutral pH i.e., pH 6.5–pH 7.5) alcohol having a titer of from about 10 to about 40% (low titer alcohol) or from about 90 to about 100% alcohol (high titer alcohol), can be used for washing CGM without extracting zein. In each of these ranges, zein is substantially insoluble. One of the advantages of this invention is that brief exposure to intermediate titers (i.e., 40–90%) can occur without substantial loss of zein. High titer alcohol washes are preferred since the quantity of alcohol required to remove colors and impurities is minimized, due to the increased solubility of the impurities. Low titers of alcohol can be used but larger quantities of alcohol are required to adequately extract the impurities. However, one advantage of using low titer alcohol is that due to the large volume of water for dilution, it is possible to reduce and/or to eliminate subsequent water washes.

The conditions which affect zein solubility in various solvents have also been described in detail by Dill, *J. Biol. Chem.* 22:239–247 (1927) and Manley, *Indus. Eng. Chem.* 35:661–665 (1943). The teachings of these papers are incorporated herein by reference.

During the pigment extraction step, zein(s) remains within the zein body membrane, which protects the alpha zein (soluble in high titer alcohol(s) such as isopropanol/ethanol) and beta zein (soluble in lower titer alcohol) fractions from being extracted along with the pigments. Under optimal conditions, zein remains encapsulated in the zein body membrane, thereby preventing zein loss. Thus, the xanthophyll/alcohol extract will remain essentially uncontaminated with zein(s) during the alcoholic extractions.

It is desirable to use high titer alcohol (i.e., 90 to 100%) for the depigmentation/deflavoring step to avoid solubilizing the zein during the extraction of pigments and contaminants. It should be noted that as the concentration of alcohol decreases (i.e., falls inside each of the curves shown in FIG. 2), the solubility of zein increases, thus resulting in the extraction of zein and overall loss of product. Preferably, alcohol washing is conducted at ambient temperature or at slightly elevated temperature. The preferred method of washing is in a continuous counter-current fashion or by batch-wise washing with fresh alcohol at each step. Either ethanol or isopropanol are the preferred solvents but can be replaced with other alcohols and food grade solvents that are miscible with water and have a limited titer range for which zein is soluble. A solvent and concentration range can be selected at which pigments and contaminants are maximally soluble and the zein is negligible or minimally soluble.

By-products of the depigmentation step, particularly xanthophyll—a yellow pigment, can be further purified using standard techniques to yield food grade food colors. Purification of the pigments can be accomplished using ion exchange resins, for example.

The xanthophyll and carotene-free corn gluten is then passed through a series of water washes to remove water-soluble products trapped by residual pigments/hydrocarbons which may not have been removed by previous wash steps, enzymatic hydrolysis and alkaline treatment of the gluten. Residual alcohol is also removed from the gluten by the water washes. The number of water washes depends upon the degree of purity desired. This can be assessed by ascertaining the amount of residual water-extractable flavor compounds removed after each washing. It should be noted that between the alcohol and water wash steps, the destarched and decolored gluten is recovered by centrifugation, filtration or freeze drying.

An alcohol extraction step is then performed to separate the gluten into a zein fraction and a protein fraction containing glutelin. During this extraction step, it is necessary to choose a concentration of alcohol and temperature at which zein is readily soluble. The preferred solvents for zein are aqueous solutions of ethanol, 2-propanol or mixtures thereof, which contain at least 40%, but less than, 90% alcohol, or the equivalent range for isopropanol. Commercial zein is typically soluble in 80:20 mixtures of 2-propanol/water in amounts up to at least 30% (v/v) protein, over a temperature range of about 5°–70° C.; and in 80:20 ethanol/water in up to at least 30% (v/v) protein, over a temperature range of about 5°–70° C., taking into account that the temperature should remain at least 5° C. below the boiling point of the solvent. For some zein applications, like film formation, it is preferable to select an alcohol titer at the upper end of the 40–90% range to minimize isolation of beta zein and glutelins and to maximize alpha zein extraction and purity. For some other applications where maximizing zein yield is most important, extractions at both high and low titers can be made and later recombined as necessary.

The yield of zein extracted can be optimized at elevated temperature (i.e., from about 25°–70° C., with 50° C. preferred) in order to facilitate extraction of the zein from remaining glutelins and zein body membrane degradation products. It is also necessary to adjust the pH of the alcoholic solution to below pH 7.0 and preferably within the range of from about 5.5 to about 6.5 to improve zein solubility. Once the pH of the ethanolic solution has been adjusted, the pH should be maintained near the isoelectric point for most zein phenotypes (i.e., from about pH 6 to about 7) to minimize extraction of marginally soluble zein(s).

In a preferred embodiment, a solution of aqueous ethanol is used containing from about 70 to about 90% ethanol; that is, having a water zethanol ratio of from about 30:70 to about 10:90. Preferably, aqueous 80% ethanol (vol) can be used for the extraction with high yield of zein.

The glutelin by-product can be recovered from the extraction cake and further purified using known techniques for use as a vegetable protein supplement. In order to achieve maximum solubility of the resultant glutelin fraction, the last zein extraction should be followed immediately by equilibrating the glutelin in <50% ethanol containing >1% humectant (based on the glutelin dry weight) chosen from the following non-limiting list or their analogs (glycerol, propylene glycol, polyethylene glycol (PEG), etc.), <2.5% gum chosen from the following list (xanthan, gelatin, konjac, alginate or its derivatives, cellulose or its derivatives, carrageenans, starch or its derivatives, locust bean gum or guar gum). Especially preferred, are the gums, like xanthan, hydroxypropylated alginate and cellulose which are soluble in alcohol at titers between 30 and 50%, i.e., which coagulate other gums and thereby inhibit uniform penetration and mixing with the glutelins. It is also desirable to incorporate a small amount (<1.25%) of food grade emulsifier into the glutelin fraction. The selection of a specific blend of these protein stabilizers will depend on the intended food application of the glutelin as a vegetable protein supplement. After formulation with the above protein stabilizers, it is preferable to dry the glutelin by-product by freeze drying. Other means for drying the product include spray drying and atmospheric drying at <50° C.

Zein can then be recovered from the alcoholic solvent and concentrated using standard techniques, such as but not limited to precipitation, ultrafiltration, evaporation or other appropriate techniques, or reduced to a dry powder by flash drying, lyophilization or spray drying. The preferred method for obtaining a readily dispersible powder is either to reduce the ethanol titer to about 15% and spray dry, or to disperse the ethanolic zein solution in a slightly alkaline (pH about 7 to 8.5), well-stirred, aqueous medium followed by gentle (<50° C. drum or standard freeze drying) dehydration to yield zein containing <10% water.

In one embodiment, zein can be further purified, depending upon end use, prior to recovering it from the alcoholic solution by passing the protein solution through a column, or an adsorbent, such as activated carbon (granular or powdered forms) and macrorecticulated resins, such as ion exchange and adsorption resins.

The purified zein produced by the methods of this invention is essentially decolored (i.e., the product is white), odor-free and deflavored. The decolored and deflavored zein is also substantially free of hydrocarbon extracts which are otherwise present using other purification techniques. Thus, purified zein produced according to the methods of this invention is suitable for use in foods and pharmaceutical applications, such as coatings, texturizers, additives and fat replacers. For example, an aqueous dispersion of deflavored and decolored zein can be cast into a continuous edible film having suitable strength and protective barrier properties. Alternatively, a film can be cast from an ethanolic solution to produce an edible barrier coating.

Prior to recovery from the alcoholic solvent, the decolored and deflavored zein can be further processed. In a preferred method, the ethanolic zein solution is injected into stirred water containing an anti-aggregate to produce water-dispersible microparticles of hydrophobic, water-insoluble zein. Such techniques are described in U.S. Pat. No. 5,021,248 (Stark and Gross), the teachings of which are incorporated herein by reference. In another embodiment, the ethanolic zein solution is dispersed as a mist before it is contacted with water, or as part of co-focused mist containing ethanolic zein and aqueous antiaggregate solutions. In each of these processes, gums and/or additive can be added to the ethanolic zein solution depending upon the desired end use.

In another embodiment of the invention, deflavored and decolored gluten, obtained after depigmentation with alcohol, can be harvested for use in foods, without additional purification or separation. For example, a concentration of 4% gluten or zein bodies (w/v) can substantially increase (>30%) the baked volume of a microwave cake without compromising its texture or taste. Deflavored and decolorized gluten also exhibits fat mimetic properties of microparticulated proteins, such as those described in U.S. Pat. No. 5,021,248, and can be used as a fat replacer and texturizer. The decolorized and deflavored gluten can be produced which contains an enriched zein body fraction (i.e., >75%). The optimum proportion of zein bodies to glutelin microparticles is dependent on the intended application. In fat replacer applications like frozen desserts, mayonnaise and whipped topping, for example, it is desirable to have an enriched gluten having >90% zein bodies. For fat replacement in sausages, however, a 50–75% incidence of the zein body fraction tends to be adequate. For microwave cake volume expansion, only a 50:50 mixture of zein bodies to glutelins produces the 30% volume expansion functionality without compromising taste or texture. Other proteins, including wheat gluten, do not have this effect. The fractionation of zein bodies and glutelin microparticles can be achieved by low speed centrifugation in alcohol, which contains aqueous alcohol soluble gum(s) and/or aqueous alcohol soluble salt(s) to effect the desired degree of zein-body enrichment. In addition, it is possible to program the sieving and gelation of the centrifugation medium by the use of a thermally reversible gelling agent (<4%) to effect the removal of the largest particles (i.e., those most likely to cause a gritty or chalky mouthfeel). The simplest application of the latter technique is to centrifuge at a temperature which maintains a relatively low viscosity (i.e., 1–400 m.Pa.S) during the centrifugal separation of the two fractions followed by lowering the temperature to below the gelling point to effect gelation and thereby prevent component mixing in the absence of a density gradient. After separation and gelation, the centrigation medium can then be sectioned and the zein body-rich fraction and glutelin-rich fraction recovered by reliquefaction (<50° C.) of the dilute gel medium. This technique is facilitated, in part, by the fact that zein is a very robust protein with respect to heat and is not readily denatured even by high temperatures (i.e., 125° C.) in glycerol.

The invention is further illustrated by the following non-limiting examples.

EXAMPLES

EXAMPLE 1

Purification of Zein

A slurry was prepared by mixing 3.3 L of deionized water with 2.8 kg of wet corn gluten meal (CGM) from representative corn wet-milling plants (Grain Processors Corp.; Muscatine, Iowa or Corn Products Corp., Argo, Ill.). The gluten is nominally 40% solids and is collected before it was dried or admixed with other process streams. The slurry was vigorously agitated with a Lightnin™ Mixer (Model TS1515, General Signal Corp., Mixing Equipment Div., USA) using a 3-inch diameter impeller to uniformly disperse the gluten. After heating the slurry to 80° C., the pH was adjusted to 6.4±0.1 using 3N sodium hydroxide.

To digest the starch, 5.1 mL of e-amylase was added to the wet gluten slurry (Taka-Therm® L-340, Solvay Enzyme Products, Inc., Elkhart, Ind.), reacted for 1 hour and then cooled to 50° C. The slurry was centrifuged in a solid bowl centrifuge at 1200 xg for 10 min and the supernatant discarded. The pellet was resuspended in an equal part of hot water-(80° C.) and centrifuged again at 1200 xg. The supernatant was discarded. No substantial reduction in off-flavor was detected when the destarched gluten was tasted.

The destarched gluten pellet was then treated with 1M sodium carbonate and 1M sodium hydrogen carbonate to adjust pH to 9.0 at 20° C. The slurry was then heated to 80° C. and found to initially produce an acrid, unpleasant odor. However, after 1 hour of agitation the headspace odor changed to a pleasant, almost sweet-smelling cereal odor. At the end of that time, the slurry was cooled to 50° C. The slurry was centrifuged in a solid bowl centrifuge at 1200 xg for 20 minutes and the supernatant discarded. The pellet was resuspended in an equal part of water and neutralized with 3N HCl. The solids were centrifuged two additional times and resuspended in an equal part of water. Even though the gluten was still bright yellow, there was no longer any offensive bitter off-taste.

The centrifuged pellet containing 599.5 g of solids was reslurried in 3 volumes of 100% (neat) ethanol at room temperature for 15 minutes. The slurry was centrifuged and the alcoholic supernatant discarded. The centrifuged pellet was resuspended five times in 2 volumes of 100% (neat) ethanol for 40 minutes. The first and second supernatants show minimal zein losses. Zein was not detected in the liquor of the third through sixth supernatants. The pellet after the sixth ethanol wash yielded 512.3 g of solids, for a loss of 11.6% throughout the ethanol washing. The successively higher alcohol titer after each wash is summarized below in Table 1.

TABLE 1

| Ethanol Wash | Estimated Ethanol Titers | % Zein* Loss |
| --- | --- | --- |
| 1 | 77.3% (wt) | 2.3 |
| 2 | 93.1% | 0.4 |
| 3 | 97.9% | — |
| 4 | 99.4% | — |
| 5 | 99.8% | — |
| 6 | 99.9% | — |

*Based on an estimated 32% zein content in the intial CGM, zein loss was determined by dropping some ethanolic wash solution into a large volume of water. Any cloud formation in the water indicated the presence of zein. It was further quantitated by measuring HPLC peak areas.

The pellet was then washed three times with 2 volumes of water and centrifuged. A small amount of zein was detected in the first and second wash waters. The total zein loss was 1.6% of the zein in the CGM starting material. The CGM cake, at this point, was grey, having lost all traces of yellow color. The fully decolored gluten was found to have no objectionable off-taste. However, a very slight residual cereal taste was still detectable and the need for its complete removal for some applications, was recognized. All washes and centrifugations were carried out at room temperature.

The water washed pellet was resuspended in an alcoholic solution calculated to raise the ethanol level in the final slurry to 80% (v/v) ethanol and permit complete dispersion of the solids. This number is a function of the pellet dry solids content. The amount of neat ethanol added to the water washed pellet was determined using the following equation:

X—volume of 100% ethanol, mL
W=wt % of pellet
Y=weight of pellet, g $$X = 3.476 * (1-(W/100)) * Y$$

If 95% ethanol was used, the equation was modified to:
Let

X=volume of 95% ethanol, mL $$X=4.661*(1-W/100))* Y.$$

The slurry was stirred and heated to 55°–60° C., the pH was adjusted to 5.9±0.1 using 1N HCl, and the extraction of zein proceeded for one hour. The resulting slurry was centrifuged and the supernatant containing zein was collected. At this stage, the pellet can be subjected to additional extractions to recover residual zein. However, it has been observed that subsequent extractions of the pellet contained a higher proportion of off-flavor compounds and required further processing to remove them.

Zein can then be recovered from the alcoholic supernatant by adding enough water to lower the final ethanol titer to less than 40% and cooling to room temperature. The resultant zein precipitate can then be recovered, dried, and ground to yield a slightly, off white, almost fully deflavored corn protein powder.

EXAMPLE 2

Further Purification Using Activated Carbon

Example 1 was repeated but before the zein was precipitated from the alcoholic suspension, it was further purified using activated carbon. Powdered carbon (Darco SGL80x325, American Norit Co., Inc., Jacksonville, Fla.) was added to the ethanolic zein liquor at 15% of the zein content. This treatment was performed at ambient temperature for one hour. The carbon powder was then filtered out using a scintered glass filter funnel and a bed of filter aid (Celite® 521, Aldrich Chemical Co., Inc., Milwaukee, Wis.). The resulting zein powder was whiter and more deflavored, after precipitation and drying than the product produced by the methods of Example 1.

EXAMPLE 3

Destarching
Method 1

An α-amylase to gluten ratio different than that of Example 1 was used to effect the hydrolysis of starch in CGM. A slurry was prepared by mixing 2.4 kg of CGM with 3.3L of deionized water. The slurry was vigorously agitated to uniformly disperse the gluten. After heating the slurry to 80° C., the pH was adjusted to 6.4±0.1 using 3N sodium hydroxide.

To digest the starch, 5.1 mL of α-amylase solution was added to the slurry (Taka-Therm® L-340, Solvay Enzyme Products, Inc., Elkhart, Ind.). Reaction time was 1 hour, after which the slurry was cooled to 50° C. Progress of the reaction was followed by periodically removing aliquots of the slurry and using an iodine indicator. Starch will form a blue or purple complex with the iodine according to the classical procedure (AOAC 925.56). At the end of one hour, there was no trace of iodine-starch complex present in the slurry.

Method 2

After starch hydrolysis according to Example 1, the slurry was centrifuged twice at 1200 xg for 20 minutes and reslurried twice with an equal part of water. All steps were carried out at ambient temperature. No substantial reduction in off-flavor was detected.

Method 3

After starch hydrolysis according to Example 1, the slurry was centrifuged at 1200 xg for 20 minutes and reslurried three times with an equal part of water. All steps were carried out at ambient temperature. No substantial reduction in off-flavor was detected.

Method 4

A slurry was prepared by mixing 1.1 kg of CGM with 2.2 L of deionized water. The starch was removed from the gluten according to the method described in Example 1. The water wash after starch digestion was not performed. Instead, the slurry was centrifuged and prepared for carbonate treatment.

Destarched gluten slurry amounting to 2.4 kg was further diluted with 2 L of deionized water. To this slurry, 240 mL of 1M sodium hydrogen carbonate and 130 mL 1M sodium carbonate were added and adjusted to pH 9.3. The slurry was then heated to 80° C. It was held at that temperature under agitation for 1 hour. At the end of that time, the slurry was cooled to 50° C. The slurry was centrifuged at 1200 xg for 20 minutes and the supernatant discarded. The pellet was resuspended in an equal part of water and neutralized with 3N HCl. The solids were twice more centrifuged and resuspended in an equal part of water. All centrifugations were performed at ambient temperature.

Centrifuged pellet containing 654.8 g of solids was reslurried in 2 volumes of 100% (neat) ethanol at ambient temperature for 15 minutes. The slurry was centrifuged and the alcoholic supernatant discarded. The pellet was resuspended seven times in 2 volumes of 100% (neat) ethanol. Each time the suspension was centrifuged, the supernatant was discarded. Two more ethanol washes were required to get to the same gray pellet color as observed using the methods of Example 1.

EXAMPLE 4

Carbonate Treatment of Destarched Wet Gluten
Method 1

Wet corn gluten was destarched according to Example 1. The destarched slurry was treated with 1M sodium carbonate and 1M sodium hydrogen carbonate to adjust pH to 8.7±0.1. The slurry was heated to 80° C. for 1 hr while agitating. The slurry was centrifuged and the supernatant discarded. The pellet was twice suspended with an equal part of water and centrifuged.

Method 2

The effect of ethanol versus water washes on the removal of off-color was evaluated. Destarched gluten was carbonate treated with 1000 mL of 10% 0.1M sodium carbonate and 90% 0.1M sodium hydrogen carbonate at 9 pH. The mixture was stirred for 1 hr at 80° C. and then cooled to room temperature. The mixture was maintained at room temperature and agitated for 3 days. The mixture was split into equal portions. The first portion was washed three times with 50% ethanol and 0.2% Tween 80. The second portion was washed three times with water. The water washed gluten, which was not exposed to either alcohol or surfactant, was much lighter in color than the (i.e., ethanol/Tween 80) ethanol/Tween 80 washed gluten (which was dark greenish brown) and also much less yellow than the destarched but not carbonated treated gluten. Water washing was therefore considered to be highly preferable to more expensive and complex methods involving alcohol and surfactants.

EXAMPLE 5

Ethanol Washing of Destarched, Carbonate Treated Gluten
Method 1

1100 mL of carbonate-treated, water-washed CGM (15% solids) prepared by the methods described in Example 1 was centrifuged, lyophilized, and resuspended in 1320 mL of absolute ethanol. The suspension was homogenized using a Polytron homogenizer to disperse the solids. The dispersion was centrifuged and the pellet was resuspended in 100% (neat) ethanol to the amount of 2 volumes of original dried cake (165 g). The alcohol washing step was repeated 6 times with 200 mL of absolute ethanol for each wash. All washes were conducted at room temperature. The ethanol washes were followed by two water washes and then the gray colored cake was reslurried in water and centrifuged at 3,000 xg for 8 min. The resultant cake was still gray but represented decolored and deflavored gluten which is suitable for some food applications.

Method 2

1 Kg of CGM was carbonate-treated, water-washed, centrifuged, and the pellet was reslurried in 3 volumes of 95% ethanol at room temperature for 2 hours. Zein loss was determined in the manner described in Example 1. Zein was not detected in the any of the supernatant ethanolic solutions, although substantial yellow pigment removal was evident. The alcoholic supernatants were then set aside for later xanthophyll pigment recovery. The centrifuge pellet was resuspended in 3 volumes of 70% ethanol for 30 minutes. Again, zein was not detected in the supernatant liquor. After centrifuging, the pellet was resuspended three more times in 1 volume of 70% ethanol. Finally, the centrifuge pellet was washed three times with 1 volume of water and centrifuged. The estimated ethanol titers during the first five washes are listed below:

| Ethanol Wash | Estimated Ethanol Titers |
|---|---|
| 1 | 78.6% (vol) |
| 2 | 71.6% |
| 3 | 70% |
| 4 | 70% |
| 5 | 70% |

Method 3

Destarched, carbonate-treated CGM produced by the methods described in Example 1, was divided into two portions. The first portion (25 g of a 29.6% solids slurry) was washed twice with 3 parts 100% (neat) ethanol. Fresh alcohol was used each time. The supernatant from the second wash was used to wash the second portion of CGM (19.3 g of the slurry). In this way, a two stage counter-current extraction was evaluated. Ethanol liquors from all three washes were analyzed by gel permeation high performance liquid chromatography (HPLC) according to the methods described below.

Solvent System:

Isocratic

60% $H_2O$/40% acetonitrile/0.1% phosphoric acid 40 minute run

Column:

Bio-Sil TSK-250 600×7.5 mm (Bio Rad)

Bio-Rad Gel Filtration Column (Catalog#125-0066)

Program:

End time—38 min

Narrowest Peak—1.4–3.2 sec

Peak Width—Automatic

Base Treatment—B to B

Area Sensitivity—1

Base Sensitivity—1

Skim Sensitivity—1

Area Rejection—either $1\times10^5$ or $1\times10^4$

Detection:

$UV\lambda=214$ mm

Dilutions:

For ethanolic zein extracts and ethanol gluten washes: A 1:1 with solvent

For UF washes—no dilution

AZTL Procedure—no dilution

Injection volume:

100 ul

The peak areas for the counter-current sample showed about a 96% zein recovery efficiency compared to the combined peak areas from the first and second fresh alcohol washes. A Summary of the alcohol washes is shown in Table 2.

TABLE 2

| | Integration Area × $10^{-6}$ | | | |
|---|---|---|---|---|
| | Fresh EtOH 1st Wash Column #1 | Fresh EtOH 2nd Wash Column #2 | Fresh EtOH 1st & 2nd Wash | Counter-Current Wash |
| Protein Area | 43.617 | .011 | 43.628 | 55.566 |
| Total Non-Protein Area | 66.052 | 12.809 | 78.861 | 76.004 |
| Total Area | 109.669 | 12.820 | 122.489 | 131.570 |

$$\text{Counter Current Wash Efficiency} = \frac{\text{Total-Protein Area For Counter Current Wash}}{\text{Total Protein Area for Fresh Wash}} = \frac{76.00}{78.86} = 96.3\%$$

EXAMPLE 6

Effect of Temperature on Color Removal 50 ml of destarched and carbonate-treated gluten cake prepared by the methods described in Example 1 (8% solids), was divided into two portions. One portion was washed (5 min) five times (40 ml each) in 100% ethanol at 25° C. The other portion was washed similarly at elevated temperature (35°–55° C.). The slurries were centrifuged at 2000 rpm for 10 minutes. The supernatants were sampled and absorbance at 450 nm measured to determine the amount of pigments extracted from the gluten cake. A final wash was done with water after the level of pigments detected in the ethanolic wash supernatant became insignificant.

Figure 3:
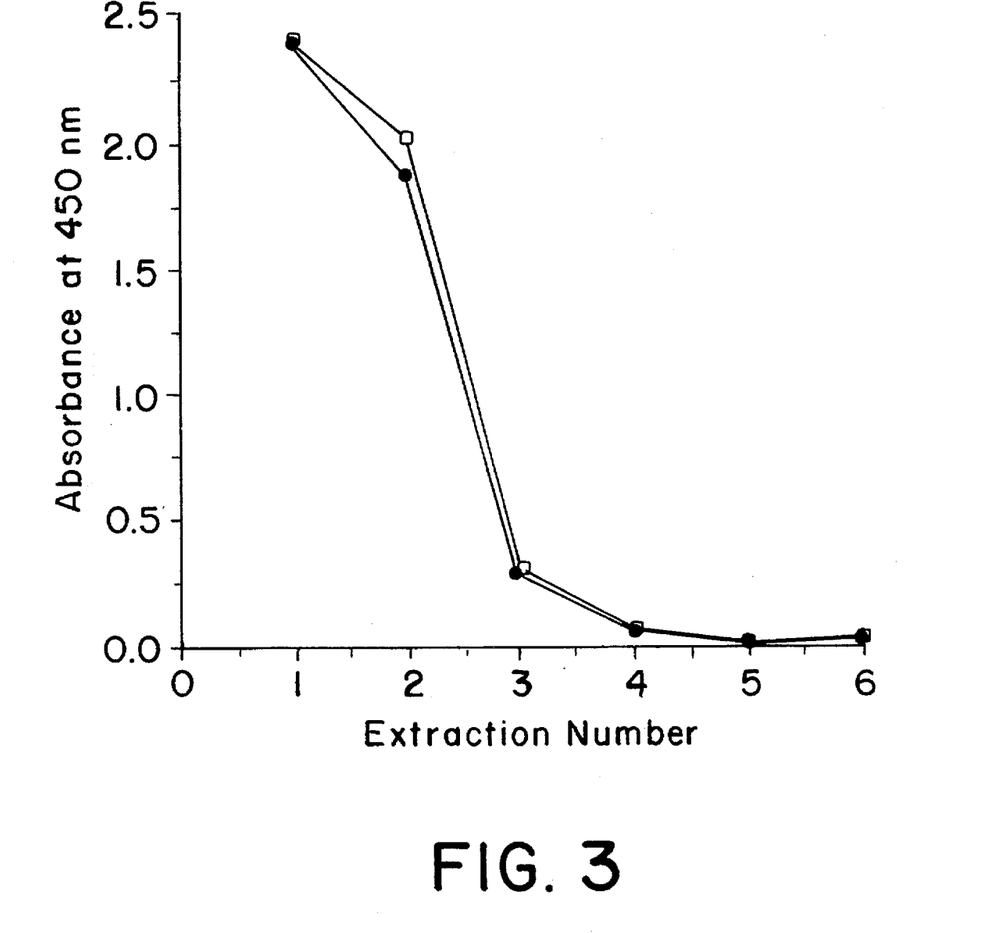
FIG. 3 shows the results from a high titer ethanol depigmentation wash. Corn gluten meal was washed with 100% Ethanol at 23° C. (□) and 45° C. (●). In the sixth extraction, water was used instead of ethanol.

The results of this pigment exaction are shown in FIG. 3 and indicate that the elevated ethanol temperature did not significantly improve the amount of pigment extracted from the gluten. The quantity of extracted pigment was essentially the same using 23° C. ethanol and 35°–55° C. ethanol.

EXAMPLE 7

Preparation of Film Forming Barrier

A zein film (9×14" ×4 mil) was cast by solvent evaporation (50° C.) from 150 mL of a 6% commercial zein (Freeman Industries, Inc., yellow granular powder) solution (80% ethanol) because a 4% solution did not adequately produce a continuous film. In contrast, only a 4% zein film cast under the same conditions from white zein made by the methods of this invention was continuous, strong and could be bent without breaking. The $O_2$, $CO_2$ and $H_2O$ barrier properties of the two films were evaluated using a Mocon analyzer (Modern Controls Inc., Minneapolis, Minn.). The results of this study are shown in Table 3.

TABLE 3

| Gas | Film Thickness (mil) | Transmission Rate cc/100 in²/24 hrs | Permeance[3] (Ave.) | OPTAZein Advantage[4] |
|---|---|---|---|---|
| $H_2O$ | | | | |
| OZ[1] | 2.0 | 10.1 | 20.5 | 32% |
| | 2.1 | 9.9 | | |
| FZ[2] | 5.5 | 5.1 | 30.2 | |
| | 3.9 | 8.3 | | |
| $CO_2$ | | | | |
| OZ | 4.1 | 3.1 | 22.3 | 53% |
| | 2.0 | 16.0 | | |
| FZ | 5.0 | 6.3 | 47.7 | |
| | 3.4 | 18.8 | | |
| $O_2$ | | | | |
| OZ | 3.9 | 5.5 | 21.9 | 26% |
| | 2.1 | 10.7 | | |
| FZ | 5.3 | 4.0 | 29.6 | |
| | 3.2 | 11.9 | | |

[1]OZ = OPTAZein produced by methods of this invention
[2]FZ = Commercial Zein 4000, Freeman Industries, Inc.
[3]Permeance determined by methods of (ASTM F-1249-90 and ASTM D-3985-81) at 23° C.
[4]The better barrier properties of the zein produced by the methods of this invention, are expressed as a % reduction in permeance relative to commercial Freeman zein 4000.

$$\left(\text{i.e., } \frac{FZ - OZ}{FZ} \times 100 = \% \text{ OPTAZein Advantage}\right)$$

The results above indicate that the film cast from 4% zein produced by the methods of this invention served as a better barrier than films cast from 6% commercial zein. It should be noted that the film produced using commercially available zein was yellow in color, in contrast to the OPTA zein film which was transparent.

EXAMPLE 8

Comparative Analysis

Figure 4:
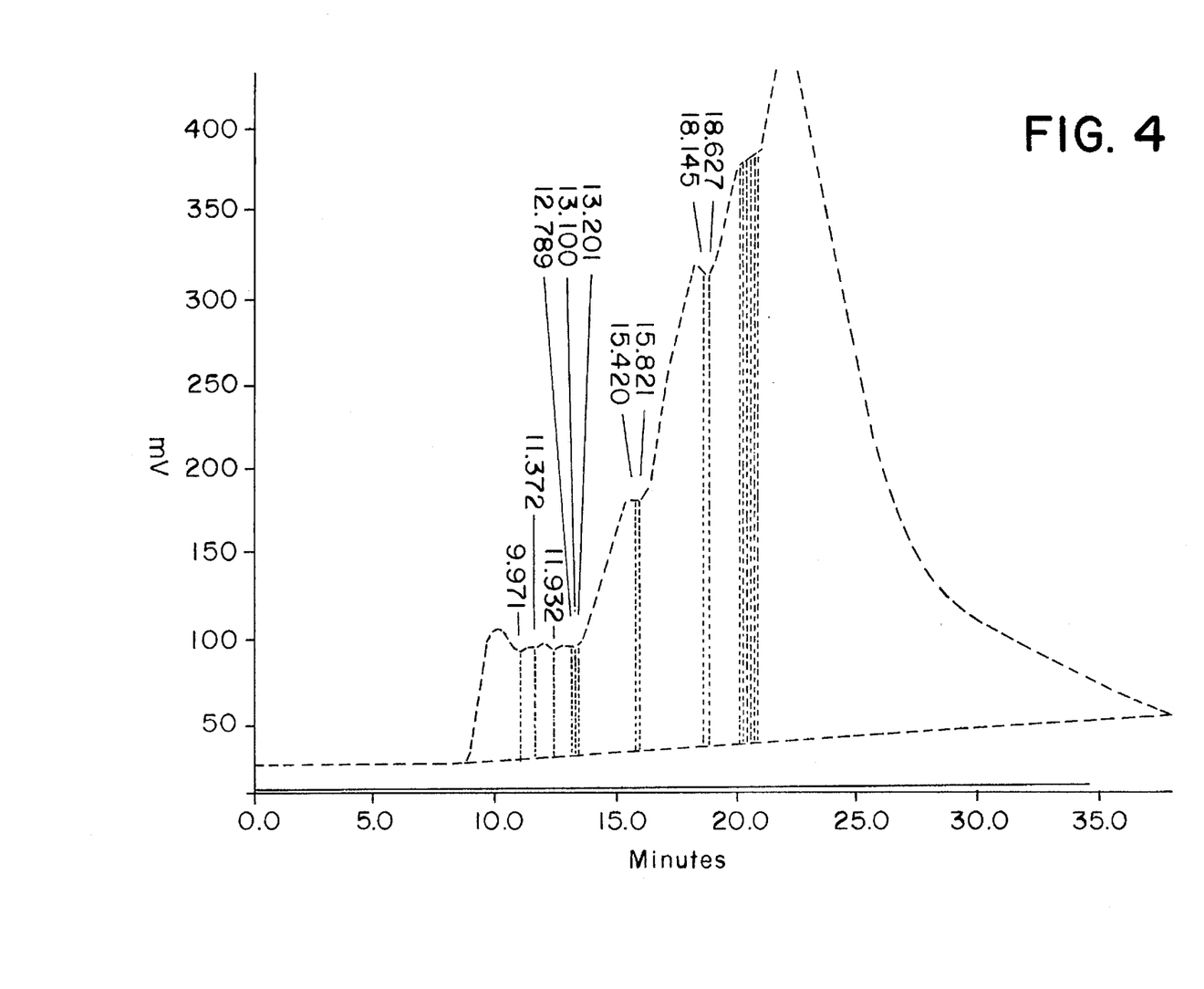
FIG. 4 shows two high performance liquid chromatograms obtained on aqueous extracts of commercial zein (Freeman Industries, Inc., Tuckahoe, N.Y.) and zein produced by the methods of this invention ((solid line just above x-axis). Commercial zein had 18 peaks with a peak area of 149.79 $\times 10^6$ units. The purified zein had zero peaks and a peak area of zero units.

The taste of the zein produced, according to the methods of this invention, was assessed by both high performance liquid chromatography (HPLC, technique described earlier) and a sensory panel using the aqueous fractions of 80% ethanolic solutions made from each type of zein. The aqueous extract was obtained by selectively evaporating the ethanol under vacuum to concentrate the water soluble organic constituents. The resultant aqueous fraction chromatograms are shown in FIG. 4.

The proximate analyses of wet gluten, destarched wet gluten, deflavored, decolored zein (hereinafter "dfdc zein") and deflavored, decolored glutelin (hereinafter "dfdc glutelin") (on a dry solids basis) and particle size distribution throughout this process are shown in Table 4.

TABLE 4

| | Proximate Analysis[1] | | | |
|---|---|---|---|---|
| | Wet Gluten[2] | Destarched Wet Gluten[2] | dfdc[2] Zein | dfdc Glutelin Cake After Zein Extraction[2] |
| Protein | 70.2% | 92.1% | 96.98 | 93.0% |
| Fat | 4.8% | 1.6% | <0.1 | 0.5% |
| Ash | 1.3% | 0.5% | 0.5 | 0.4% |
| Total | 23.7% | 5.8% | 2.51 | 6.0% |

TABLE 4-continued

| | Proximate Analysis[1] | | | |
|---|---|---|---|---|
| | Wet Gluten[2] | Destarched Wet Gluten[2] | dfdc[2] Zein | dfdc Glutelin Cake After Zein Extraction[2] |
| Carbohydrate Dietary Fiber | 8.1% | 5.8% | n.d.[3] | n.d.[3] |

[1]A.O.A.E., 15th Edition Method 981.10 (1990).
[2]determined on an anhydrous basis
[3]n.d. — not determined Table 4 illustrates the increasing percentage of protein typically achieved by the invention as one proceeds from the wet gluten starting material to the intermediate destarched wet gluten and finally to the dfdc zein and dfdc glutelin. It should be noted that the standard proximate analysis technique does not specifically determine carbohydrate (i.e., using phenol, anthrone or other carbohydrate-specific reagents. Instead, the protein nitrogen was specifically determined using a micro Kjeldahl technique. Kjeldahl Test, pg 674, Hawley's Condensed Chem. Dictionary, 11th Ed. (1987) Van Nostrams, Reinhold, N.Y. The fat was determined by extraction in ether and the ash content was determined gravimetrically using an ashing furnace. The appropriate factor for nitrogen in the micro Kjeldahl calculation to convert to % protein is a function of the amino acid content of the protein sample. When analyzing for the largest component in the sample (i.e., protein), small changes in the % nitrogen to % protein conversion factor can make significant differences in the protein purity determination. For example, in the case of dfdc zein, the ash (which was specifically determined), and the fat (which was determined by extraction) are $\leq 0.6\%$ by weight of the sample, it is possible that the protein content could be 99.4% (i.e., adding 2.51% to 96.98%) instead of 96.08% depending upon the conversion factor used. Such a conclusion would require a precise determination of the sampler's amino acid content and appropriate change in the Kjeldahl nitrogen factor.

EXAMPLE 9

Zein Body and Glutelin Microparticle Isolation

One of the principal advantages of the invention is that it preserves the natural microparticulation of its zein body and glutelin components as shown in the "Median Size" Column in Table 5 below:

TABLE 5

| Process Step | Mean Size (μm) | Median Size (μm) | 10% Size (μm) | 90% Size (μm) |
|---|---|---|---|---|
| Feed Gluten | 15.86 | 10.29 | 4.87 | 35.25 |
| After Amylase | 13.85 | 8.48 | 3.93 | 31.32 |
| After Carbonate | 8.97 | 6.17 | 2.95 | 15.41 |
| After 1st EtOH Wash | 17.45 | 8.43 | 3.85 | 45.68 |
| After 2nd EtOH Wash | 13.1 | 7.63 | 3.40 | 31.09 |
| After 6th EtOH Wash | 21.21 | 8.75 | 3.47 | 60.98 |
| After 3rd $H_2O$ Wash | 23.30 | 9.92 | 3.76 | 66.30 |

If the median particle size is used as an index, then the original gluten particle size distribution is essentially unchanged during processing. The rise in mean size and 90 percentile values is due to some agglomeration.

After isolation of the dfdc gluten, in either wet or gently dried forms (preferably containing a humectant), the zein body and glutelin components can be isolated by centrifugation using one of the methods below. The specific method chosen will typically depend more on the intended food application than on any other factor.

The isolation of zein bodies from native corn endosperm—as opposed to wet milled gluten, has been reported using 15% sucrose gradients which are impractical for commercial use. Instead, it has now been discovered that the centrifugal isolation of zein body-rich and glutelin-rich fractions which meet commercial food needs is possible using a combination of viscosifying gums and salting out techniques. Method 1 illustrates the principle for aqueous separations while Method 2 illustrates a conceptually similar separation in an alcohol solvent of varying titer.

Method 1

Aqueous Dispersion of dfdc Gluten

A 20% (w/v) suspension (25° C.) of dfdc gluten was prepared in water or taken as an appropriate dilution of the last water wash in Example 1. It was mixed 1:1 with a 2% suspension of a suitable gum (listed earlier) and cooled after dissolving to 25° C. Thus, 10 g (dry solids equivalent) of dfdc gluten was suspended in 50 ml of distilled or deionized water and homogenized briefly (10,000 rpm, 1 min) in a Polytron homogenator. The resultant suspension was combined with 50 ml of 2% xanthan gum in water and the two are mixed at low speed (<500 rpm) for 5 min. The gluten suspension was divided between two 50 mL plastic centrifuge tubes and centrifuged for 5 min at approx. 2000 rpm and the relative enrichment of the two fractions was monitored using a microscope (1200×magnification). This non-equilibrium separation permitted recovery of a zein body-rich fraction ($\geq 75\%$ zein bodies in the supernatant and a glutelin-rich fraction in the precipitated or heavier fraction). If the separation is inadequate, additional centrifugation under the above conditions can be done. Addition of divalent salts (e.g., calcium salts), adjustment of the pH to the pI of the glutelin microparticles (determined by zein potential measurement in free-flowing electrophoresis), and/or ammonium sulfate precipitation can further facilitate isolation or fraction-enrichment.

Method 2

Ethanolic Dispersion of dfdc Gluten

Since there are alcohol titers (and pHs) which zein is not extracted from the zein bodies, it is possible to separate the two fractions by centrifugation in various titers of alcohol. When 70–100% titers of alcohol are used, it is important to add some suitable humectant (<1%; described above) to prevent dehydration of the protein, aggregation and other adverse textural effects.

A 10% (w/v) suspension of dfdc gluten was prepared in either high titer ethanol (85–100%) or low titer ethanol (0–55%). In this instance, a 95% ethanol titer was used containing 2% CaOAC (which is an alcohol soluble salt) and 5% glycerol, 50 ml of the CaOAC/glycerol/xanthan-containing ethanol was added to the 50 mL of 20% gluten suspension and centrifuged for 10 min. at 50 rpm. The resultant separation was monitored microscopically (800–1000X) and additional centrifugations were performed if the incidence of zein body purity was less than desired.

The fractions were separated by decanting the light zein body-rich supernatant which represents approximately 50% of the dfdc gluten weight. Since the zein body fraction, thus isolated appears to be 95% pure, this represents a 50% yield of the total zein bodies in the gluten. Since such separations are possible in both aqueous and alcoholic fluids, it is likely that an analogous separation could be effected in a suitable air classification apparatus (i.e., hydroclone, etc.).

EQUIVALENTS

Those skilled in the art will recognize, or be able to ascertain using no more than routine experimentation, many equivalents to the specific embodiments of the invention described herein. Such equivalents are intended to be encompassed by the following claims:

We claim:

1. Edible, decolored and deflavored zein or zein bodies produced by a process comprising the steps of removing color and flavor impurities from corn gluten by treating corn gluten with alkali to remove fatty acids and corn oils contained therein and then with an aqueous alcoholic solvent having a concentration which does not substantially extract zein and zein bodies therefrom, thereafter changing the concentration of the alcoholic solvent to a concentration sufficient to separate the gluten into decolored and deflavored zein or zein bodies fractions that are free of corn oils, xanthophyll and fatty acids.

2. Edible, decolored and deflavored zein or zein bodies produced by a process comprising the steps of:
   a) destarching corn gluten with a carbohydrate hydrolyzing enzyme under agitating conditions, sufficient to hydrolyze and remove starch contained therein;
   b) treating the destarched corn gluten of step (a) with an alkaline buffer having a pH from about 7.5 to about 9 under conditions sufficient to remove fatty acids or corn oils contained therein;
   c) selectively extracting pigments and flavor compounds from the destarched and alkaline treated gluten of step (b) with aqueous alcohol having an alcohol concentration that does not substantially extract zein or zein bodies;
   d) separating the gluten into zein or zein body and glutelin fractions by extracting or fractionating the gluten of step (c) with aqueous alcohol solvent having an alcohol concentration sufficient to either solubilize the zein or fractionate zein bodies therein; and
   e) recovering the separated zein or zein body fractions from the appropriate aqueous alcoholic medium to thereby yield decolored and deflavored zein or zein bodies containing zein therein that are free of corn oils, xanthophyll and fatty acids.

3. An edible, continuous film cast from an ethanolic solution or an aqueous dispersion containing decolored and deflavored zein of claim 2.

4. An ethanol solution containing edible deflavored and decolored zein of claim 2, which solution is suitable for use as an edible barrier coating.

5. An edible, decolored and deflavored zein that is suitable for use in a food or pharmaceutical application, and that is free of corn oils, fatty acids and xanthophyll.

6. A food product containing edible, decolored and deflavored zein, zein bodies or combinations thereof as a fat replacer or texturizer in the food product.

7. An aqueous suspension containing edible, decolored and deflavored zein bodies, which suspension is suitable for use as an edible barrier coating.

8. An ethanolic solution or aqueous suspension containing edible, decolored and deflavored zein, which solution or suspension is suitable for use as an edible barrier coating.

9. An edible, continuous film cast from an ethanolic solution or an aqueous suspension containing edible, decolored and deflavored zein.

10. An edible, continuous film cast from an aqueous suspension of edible, decolored and deflavored zein bodies.

11. Edible, deflavored and decolored zein bodies that are suitable for use in a food or pharmaceutical application.

12. A pharmaceutical product containing edible, decolored and deflavored zein, zein bodies or combinations thereof.

13. A food or pharmaceutical which is coated with edible, decolored and deflavored zein, zein bodies or combinations thereof.

* * * * *